US00PP37475P3

(12) United States Plant Patent
Schoone

(10) Patent No.: US PP37,475 P3
(45) Date of Patent: Jun. 16, 2026

(54) ***PHALAENOPSIS* PLANT NAMED 'Spin Doctor'**

(50) Latin Name: *Phalaenopsis hybrida*
Varietal Denomination: Spin Doctor

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 19/354,782

(22) Filed: Oct. 9, 2025

(65) Prior Publication Data

US 2026/0123561 P1 Apr. 30, 2026

Related U.S. Application Data

(60) Provisional application No. 63/714,593, filed on Oct. 31, 2024.

(51) Int. Cl.

| | |
|---|---|
| ***A01H 5/02*** | (2018.01) |
| ***A01H 5/00*** | (2018.01) |
| ***A01H 6/62*** | (2018.01) |

(52) U.S. Cl.
USPC ..... Plt./311
CPC ..... *A01H 6/62* (2018.05); *A01H 5/00* (2013.01)

(58) Field of Classification Search
USPC ..... Plt./311
See application file for complete search history.

(56) References Cited

U.S. PATENT DOCUMENTS

PP33,925 P3 * 2/2022 Schoone ..... A01H 6/62
Plt./311

* cited by examiner

*Primary Examiner* — Susan Mccormick Ewoldt
*Assistant Examiner* — Zachariah Allan Kay
(74) *Attorney, Agent, or Firm* — C. Anne Whealy

(57) ABSTRACT

A new and distinct cultivar of *Phalaenopsis* plant named 'Spin Doctor', characterized by its upright plant habit; moderately vigorous growth habit; strong flowering stems; healthy and sturdy leaves; freely flowering habit with typically two inflorescences developing per plant, each inflorescence with numerous flowers; flower petals and sepals that are white in color with a dark reddish purple to purplish red-colored spotted pattern that radiates from the center of the flower; and good postproduction longevity.

2 Drawing Sheets

Figure 1:
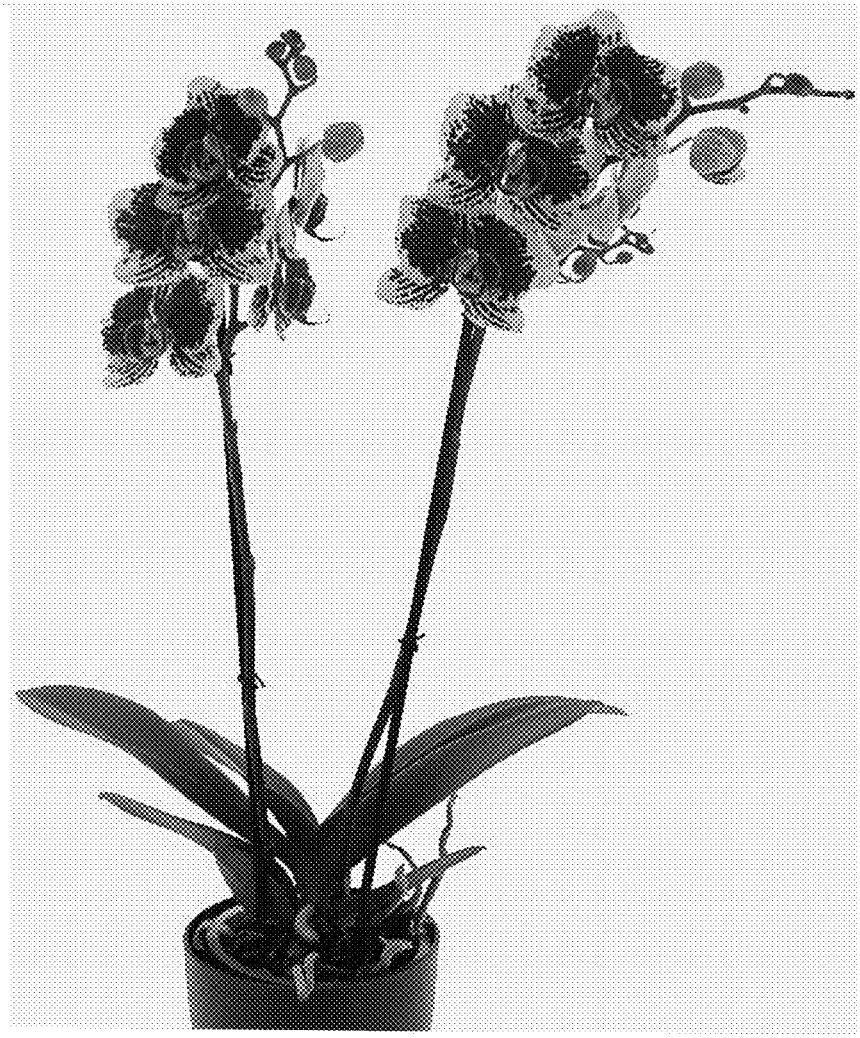

Botanical designation: *Phalaenopsis hybrida.*
Cultivar denomination: 'SPIN DOCTOR'.

CROSS-REFERENCED TO CLOSELY-RELATED APPLICATIONS

A European Community Plant Breeder's Rights application for the instant plant was filed by the Applicant/Assignee, Floricultura B.V. of Heemskerk, The Netherlands on Dec. 4, 2024, application number 2024/3020. Foreign priority is not claimed to this application.

BACKGROUND OF THE INVENTION

The present invention relates to a new and distinct cultivar of *Phalaenopsis* plant, botanically known as *Phalaenopsis hybrida*, and hereinafter referred to by the name 'Spin Doctor'.

The new *Phalaenopsis* plant is a product of a planned breeding program conducted by the Inventor in Heemskerk and Assendelft, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in May, 2014 in Heemskerk, The Netherlands of *Phalaenopsis hybrida* 'Fureshing Speckle', not patented, as the female, or seed, parent with *Phalaenopsis hybrida* 'Chain Xen Violin', not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in October, 2020.

Asexual reproduction of the new *Phalaenopsis* plant by in vitro meristem propagation in a controlled environment in Assendelft, The Netherlands since November, 2021 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Spin Doctor'. These characteristics in combination distinguish 'Spin Doctor' as a new and distinct *Phalaenopsis* plant:

1. Upright plant habit.
2. Moderately vigorous growth habit.
3. Strong flowering stems.
4. Healthy and sturdy leaves.
5. Freely flowering habit with typically two inflorescences developing per plant, each inflorescence with numerous flowers.
6. Flower petals and sepals that are white in color with a dark reddish purple to purplish red-colored spotted pattern that radiates from the center of the flower.
7. Good postproduction longevity.

Plants of the new *Phalaenopsis* can be compared to plants of the female parent, 'Fureshing Speckle'. Plants of the new *Phalaenopsis* differ primarily from plants of 'Fureshing Speckle' in the following characteristics:

1. Petals and sepals of plants of the new *Phalaenopsis* have a white ground color whereas petals and sepals of plants of 'Fureshing Speckle' have a purplish red ground color.
2. Petals and sepals of plants of the new *Phalaenopsis* have fewer spots than petals and sepals of plants of 'Fureshing Speckle'.

Plants of the new *Phalaenopsis* can be compared to plants of the male parent, 'Chain Xen Violin'. Plants of the new *Phalaenopsis* differ primarily from plants of 'Chain Xen Violin' in the following characteristics:

1. Petals and sepals of plants of the new *Phalaenopsis* have a white ground color whereas petals and sepals of plants of 'Chain Xen Violin' have a purplish red ground color.
2. Petals and sepals of plants of the new *Phalaenopsis* have fewer spots than petals and sepals of plants of 'Chain Xen Violin'.

Plants of the new *Phalaenopsis* can be compared to plants of x *Phalaenopsis hybrida* 'Secret Messages', disclosed in U.S. Plant Pat. No. 33,925. In side-by-side comparisons, plants of the new *Phalaenopsis* differ primarily from plants of 'Secret Messages' in the following characteristics:

1. Petals and sepals of plants of the new *Phalaenopsis* have fewer individual (separate) spots than petals and sepals of plants of 'Secret Messages'.
2. Cirrhose apices of plants of the new *Phalaenopsis* are shorter than cirrhose apices of plants of 'Secret Messages'.
3. Peduncles of plants of the new *Phalaenopsis* typically do not have any anthocyanin coloration whereas peduncles of plants of plants of 'Secret Messages' have a moderate amount of anthocyanin coloration.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Spin Doctor' grown in a container.

Figure 2:
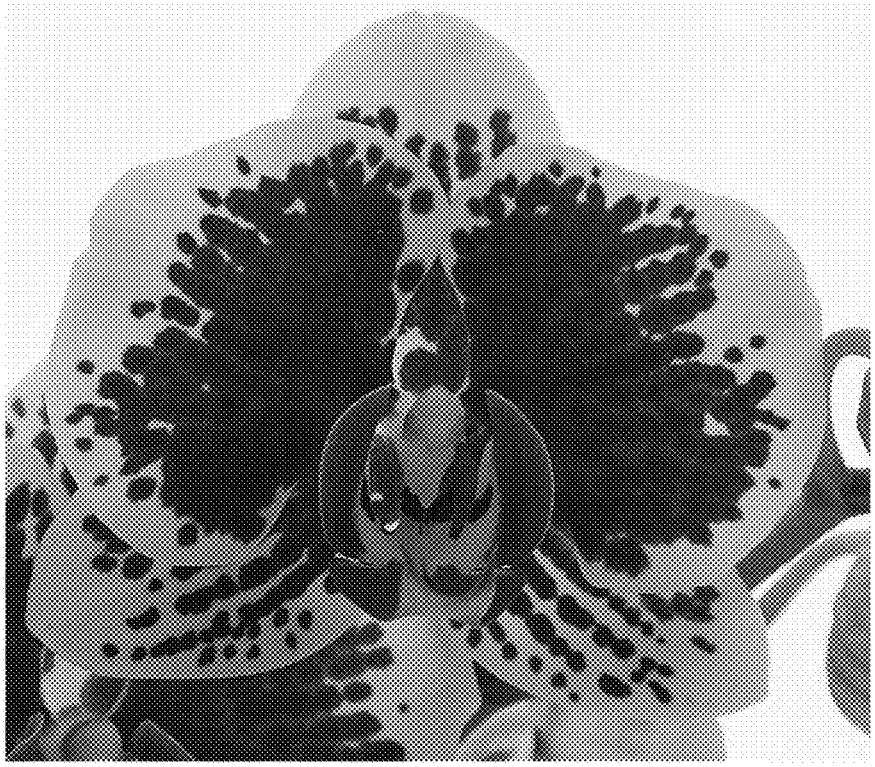

The photograph on the second sheet (FIG. 2) is a close-up view of a typical flower of 'Spin Doctor'.

DETAILED BOTANICAL DESCRIPTION

The aforementioned photographs and following observations and measurements describe plants grown during the winter in 11-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final months of production of the plants, day temperatures ranged from 20° C. to 22° C. and night temperatures ranged from 18° C. to 20° C. During the production of the plants, light levels ranged from a minimum of 5 klux to a maximum of 10 klux. In the following description, color references are made to The Royal Horticultural Society Colour Chart, 2015 Edition, except where general terms of ordinary dictionary significance are used.

Botanical classification: *Phalaenopsis hybrida* 'Spin Doctor'.

Parentage:

*Female, or seed, parent.*—*Phalaenopsis hybrida* 'Fureshing Speckle', not patented.

*Male, or pollen, parent.*—*Phalaenopsis hybrida* 'Chain Xen Violin', not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thin, fibrous; typically light yellowish white in color; actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; upright plant habit with typically two inflorescences developing per plant, each inflorescence with numerous flowers; monopodial; moderately vigorous and moderate growth rate.

*Plant height, substrate level to top of foliar plane.*—About 14.7 cm.

*Plant height, substrate level to top of floral plane.*—About 43.8 cm.

*Plant diameter or spread.*—About 30.1 cm.

Leaf description:

*Arrangement and quantity.*—Distichous, simple; sessile; about four to six fully-developed leaves per plant.

*Length.*—About 18.7 cm.

*Width.*—About 5.9 cm.

*Aspect.*—Semi-erect to horizontal.

*Shape.*—Oblanceolate to oblanceolate-oblong; moderately carinate.

*Apex.*—Acute to unequal acute.

*Base.*—Sheathing. Sheath length: About 1.9 cm. Sheath width: About 1.3 cm. Sheath color, upper and lower surfaces: Close to 143C.

*Margin.*—Entire.

*Texture and luster, upper and lower surfaces.*—Smooth, glabrous; slightly glossy.

*Venation pattern.*—Camptodromous.

*Color.*—Developing leaves, upper surface: Close to 146A; narrow marginal edges, close to 144B and 144C. Developing leaves, lower surface: Close to a blend of 146A and 146B; narrow marginal edges, close to 144B and 144C. Fully expanded leaves, upper surface: Close to a blend of 137B and 146B; narrow marginal edges, close to 144B; venation, close to 147A. Fully expanded leaves, lower surface: Close to a blend of 138A and 147B; narrow marginal edges, close to 144B; venation, close to NN137C.

Inflorescence description:

*Appearance and flowering habit.*—Showy zygomorphic flowers arranged on axillary simple or branched racemes; typically two inflorescences develop per plant; each inflorescence with about 13 flowers; flowers face mostly outwardly on outwardly arching inflorescences supported by upright peduncles; flowers with three petals, two lateral petals and one center petal transformed into a labellum and three sepals.

*Fragrance.*—None detected.

*Time to flower.*—Plants begin flowering about six months after planting; plants flower naturally during the winter into the spring.

*Flower longevity and postproduction longevity.*—Long flowering period and good postproduction longevity, individual flowers maintain good substance for about seven weeks on the plant; flowers not persistent.

*Inflorescence length* (*lowermost flower to inflorescence apex*).—About 21.4 cm.

*Inflorescence width.*—About 14.5 cm.

*Flower buds* (*about one week before flower opening*).—Height: About 2.1 cm. Diameter: About 1.6 cm. Shape: Broadly ovoid. Color: Close to a blend of 145A, 145B and 151D; towards the base, close to 145A; venation, close to 197B.

*Flower size.*—About 7.2 cm (vertical) by 8 cm (horizontal).

*Flower depth.*—About 3.3 cm.

*Petals, quantity and arrangement.*—Three, two lateral petals and one center petal transformed into a labellum.

*Lateral petals.*—Length: About 3.9 cm. Width: About 4.9 cm. Shape: Broadly reniform to deltoid; not imbricate. Apex: Shallowly retuse. Margin: Entire; slightly undulate. Texture and luster, upper and lower surfaces: Smooth, glabrous; moderately velvety; matte. Color: When opening, upper surface: Close to NN155B to NN155C; towards the base, close to 155C; following the veins, dense blotches, close to N79C and N186D and moderately dense dots, close to 197C. When opening, lower surface: Close to NN155C; towards the base, close to NN155B; following the veins, dense blotches, close to N187C to N187D; at the center, close to 85D. Fully opened, upper surface: Close to NN155D; following the veins, dense blotches, close to NN78A and N79C and sparse dots, close to 197C. Fully opened, lower surface: Close to NN155D; following the veins, dense blotches, close to N187C to N187D; at the center, close to 85D.

*Labella.*—Appearance: Three-parted with two lateral lobes and a central lobe. Length, lateral lobes: About 1.9 cm. Width, lateral lobes: About 1.4 cm. Length, central lobe: About 2.2 cm. Width, central lobe: About 0.7 cm to 2 cm. Length, cirrhose apices: About 6 mm. Shape, lateral lobes: Broadly obovate. Shape, central lobe: Deltoid. Apex, lateral lobes: Obtuse. Apex, central lobe: Cleft with two cirrhose apices curled upwards and backwards. Margins, lateral and central lobes: Entire. Texture and luster, lateral and central lobes, upper and lower surfaces: Smooth, glabrous, velvety; matte. Callosities: Located at the base of the labellum and attachment point of the lateral petals; about 4 mm in length, about 5 mm in width and about 5 mm in height. Color, lateral lobes: When opening, upper surface: Close to 64A; towards the apex, close to 64B; at the base, close to NN155C; blotches, close to N186C and a small basal blotch, close to 4A. When opening, lower surface: Close to 64B and 187D; at the base, close to 155A; blotches, close to N187D. Fully opened, upper surface: Close to 64A; towards the apex, close to 71B to 71D; at the base, close to NN155C; blotches, close to N186C and a small basal blotch, close to 4A. Fully opened, lower surface: Close to 64B; at the base, close to 155A; blotches, close to N187D. Color, central lobe: When opening, upper surface: Close to 64A; towards the apex, close to 64C; apical margins, close to 1B; at the base, close to 187A and NN155D; cirrhose apices, close to 64C. When opening, lower surface: Close to 64A and 64B; center, close to 155C; towards the apex, close to 75A; apical margins, close to 1C; at the base, close to N155A; cirrhose apices, close to 64B. Fully opened, upper surface: Close to 64A; towards the apex, close to 64C fading to closer to 72C; apical margins, close to 5B; at the base, close to 187A and NN155D; cirrhose apices, close to 72A. Fully opened, lower surface: Close to 64A and 64B; center, close to 155C; towards the apex, close to 75A; apical margins, close to 3B; at the base, close to N155A; cirrhose apices, close to 64B. Color, callosities: When developing: Close to 150D; towards the apex, close to N186C; blotch, close to 4B. Fully developed: Close to 155C; towards the apex, close to N186C; blotch, close to 4C.

*Sepals.*—Quantity and arrangement: Three, one upper dorsal sepal and two lower lateral sepals. Length, dorsal sepal: About 4.3 cm. Width, dorsal sepal: About 2.9 cm. Length, lateral sepals: About 4.3 cm. Width, lateral sepals: About 2.5 cm. Shape, dorsal sepal: Obovate. Shape, lateral sepals: Ovate. Apex, dorsal sepal: Retuse to emarginate. Apex, lateral sepals: Bluntly acute. Base, dorsal and lateral sepals: Cuneate. Margins, dorsal and lateral sepals: Entire. Texture and luster, dorsal and lateral sepals, upper surface: Smooth, glabrous; moderately velvety; matte. Texture and luster, dorsal and lateral sepals, lower surface: Smooth, glabrous; slightly velvety; slightly glossy. Color, dorsal sepal: When opening, upper surface: Close to NN155D; following the veins, dense blotches, close to 71A, N79C and N186D. When opening, lower surface: Close to a blend of 145D and 150D; towards the apex and margins, close to 155C; along the margins, blotches, close to a blend of N77C, N187C and N187D; venation, close to 146D. Fully opened, upper surface: Close to NN155D; following the veins, dense blotches, close to 72A, 72B and N97C. Fully opened, lower surface: Close to 157C and 157D; towards the apex and margins, close to NN155D; along the margins, blotches, close to a blend of N77D, N187C and N187D; venation, close to N187D. Color, lateral sepals: When opening, upper surface: Upper half, close to 157D with dense blotches following the venation, close to 71A and N186D; lower half, close to 157A with dense blotches following the venation, close to 187A and 187B. When opening, lower surface: Close to 145B to 145D; towards the margins, close to 157A to 157D; along the margins, blotches, close to N187C; venation, close to 146D. Fully opened, upper surface: Upper half, close to 155C with dense blotches following the venation, close to 72A, 72B and N79C; lower half, close to 157D with dense blotches following the venation, close to 187A, 187B and N186C. Fully opened, lower surface: Close to 145C; towards the margins, close to 155C; along the margins, blotches, close to a blend of N77D, N187C and N187D; venation, close to 146D.

*Peduncles*.—Length: About 46.7 cm. Diameter: About 5 mm. Strength: Strong. Aspect: Upright to outwardly arching. Texture and luster: Smooth, glabrous; matte. Color: Close to 147B; densely covered with fine dots, close to 145C and 145D.

*Pedicels*.—Length: About 3.4 cm. Diameter: About 4 mm. Strength: Moderately strong. Aspect: About 65° from peduncle axis. Texture and luster: Smooth, glabrous; matte. Color: Close to 144D; distal end, close to 150D; proximal end, close to 197A.

*Reproductive organs*.—Androecium: Column length: About 9 mm. Column width: About 6 mm. Column color: Close to N78B; at the apex, tinged with close to 155C; at the base, close to NN155B. Pollinia quantity: Two. Pollinia diameter (per two pollinia): About 2 mm. Pollinia color: Close to 24A. Gynoecium: Stigma length: About 4 mm. Stigma width: About 5 mm. Stigma shape: Reniform. Stigma color: Close to N155A. Ovary length: About 1.2 cm. Ovary diameter: About 1 mm. Ovary color: Close to 150C. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'Spin Doctor' as herein illustrated and described.

* * * * *